(12) United States Patent
Kanteepan et al.

(10) Patent No.: US 10,314,880 B2
(45) Date of Patent: Jun. 11, 2019

(54) COMPOSITION COMPRISING BORTEZOMIB

(71) Applicant: FTF Pharma Private Limited, Ahmedabad, Gujarat (IN)

(72) Inventors: P. Kanteepan, Gujarat (IN); Sagar Laxmanbhai Vekariya, Gujarat (IN); Jayanta Kumar Mandal, Gujarat (IN); Sandip P. Mehta, Gujarat (IN)

( * ) Notice: Subject to any disclaimer, the term of this patent is extended or adjusted under 35 U.S.C. 154(b) by 74 days.

(21) Appl. No.: 15/230,310

(22) Filed: Aug. 5, 2016

(65) Prior Publication Data

US 2017/0035831 A1 Feb. 9, 2017

(30) Foreign Application Priority Data

Aug. 6, 2015 (IN) .......................... 2968/MUM/2015

(51) Int. Cl.
| | |
|---|---|
| *A61K 38/05* | (2006.01) |
| *A61K 9/00* | (2006.01) |
| *A61K 47/22* | (2006.01) |
| *A61K 47/10* | (2017.01) |
| *A61K 47/20* | (2006.01) |
| *A61K 9/08* | (2006.01) |

(52) U.S. Cl.
CPC ............ *A61K 38/05* (2013.01); *A61K 9/0019* (2013.01); *A61K 47/10* (2013.01); *A61K 47/20* (2013.01); *A61K 47/22* (2013.01); *A61K 9/08* (2013.01)

(58) Field of Classification Search
None
See application file for complete search history.

(56) References Cited

U.S. PATENT DOCUMENTS

2011/0178470 A1* 7/2011 Kocherlakota ...... A61K 9/0019
604/187
2012/0172808 A1* 7/2012 Soppimath ........... A61K 9/0019
604/187

FOREIGN PATENT DOCUMENTS

CN 102784114 * 11/2012

OTHER PUBLICATIONS

Sodium carbonate entry (retrieved from https://pubchem.ncbi.nlm.nih.gov/compound/sodium_carbonate#section=Top on Oct. 24, 2017, 1 page) (Year: 2017).*
Translation of CN102784114 Nov. 21, 2012 retrieved from http://www.google.com/patents/CN102784114A?cl=en on Oct. 24, 2017, 6 pages (Year: 2012).*

* cited by examiner

*Primary Examiner* — Karlheinz R. Skowronek
*Assistant Examiner* — Ronald T Niebauer
(74) *Attorney, Agent, or Firm* — Don D. Cha; HDC IP Law, LLP

(57) ABSTRACT

The present invention relates to ready to dilute injectable formulations of bortezomib comprising bortezomib, non-aqueous solvents enhancing the solubility and pH modifying agent.

7 Claims, No Drawings

COMPOSITION COMPRISING BORTEZOMIB

FIELD OF THE INVENTION

The present invention pertains to the field of pharmaceutical composition of bortezomib. In particular, present invention relates to ready to dilute injectable formulations of bortezomib comprising bortezomib, non-aqueous solvents enhancing the solubility and pH modifying agent. Further, present invention relates to the process of preparation of ready to dilute injectable bortezomib formulations.

BACKGROUND OF THE INVENTION

The high price of many innovative drugs, which is in part due to costs, time and risks involved in drug development, calls for more efficient approaches to bring drugs to the market. Translational research has been identified as an important component of such strategies. Translational research is not only a function of quality science but also the collaboration of academia and industry, which is best exemplified by success history of bortezomib.

Dipeptide boronate named MG-341 was designed by a straightforward medicinal chemistry approach. Bortezomib was first described in U.S. Pat. No. 5,780,454 with the code MG-341. Because of being proteosome inhibitor, bortezomib is involved in inflammatory responses via activation of NF-kB.

WO 99015183 discloses a method of treatment of inflammatory and autoimmune diseases by administering proteosome inhibitors.

Bortezomib worked very well in animal models of inflammation, especially in rheumatoid arthritis after phase I trial. After phase II trial, multiple myeloma found to be more susceptible to bortezomib based on the study of bortezomib in which bortezomib removed all signs of cancer in a patient of advanced stages of multiple myeloma. Thus, bortezomib was approved by FDA as an injectable small molecule for the treatment of multiple myeloma.

Bortezomib, [(1R)-3-methyl-1-[[(2s)-3-phenyl-2-(pyrazine-2-carbonylamino)propanoyl]amino]butyl]boronic acid, is the first therapeutic anti-neoplastic proteosome inhibitor. Bortezomib is a modified dipeptidyl boronic acid derived from leucine and phenylalanine. Bortezomib works via inhibition of proteolytic activity of proteosome and thus it inhibit degradation of poly-ubiquitinated proteins responsible for catalysis of proteins.

Bortezomib is isolated as trimeric boroxine. Bortezomib as such has poor water solubility, so to overcome this difficulty various dosage forms are formulated.

U.S. Pat. Nos. 6,958,319 and 6,713,446 discloses stable pharmaceutical compositions of boronic acid compounds which are prepared by lyophilization of an aqueous mixture comprising a boronic acid compound and a moiety derived from sugar produces a stable composition that readily releases the boronic acid compound upon dissolution in aqueous media.

U.S. Pat. No. 6,699,835 discloses lyophilized powder form of bortezomib with D-mannitol.

US20110178470 discloses oral and parenteral formulations of bortezomib or its pharmaceutically acceptable salts or solvates, in the form of ready-to-use solution, lyophilized forms or physical admixtures. This patent further discloses processes for preparation of these compositions and methods of using compositions for treating various types of cancers in mammals.

WO2010089768 discloses a bortezomib formulation in which bortezomib is lyophilized with tromethamine.

WO20100114982 discloses lyophilized cake formulation of bortezomib containing bortezomib, cyclodextrin, bulking agent and surfactant.

US20110230441 discloses multi-dose formulation of bortezomib with improved stability, wherein bortezomib is in liquid form suitable for injection with propylene glycol solvent.

US20120083457 discloses lyophilized composition of bortezomib and boric acid in a mass ratio of boric acid to bortezomib is from 1:1 to 10:1.

EP2644189 discloses storage-stable multi-dose liquid formulation of bortezomib with improved stability.

Existed lyophilized products have several disadvantages which includes time consuming reconstitution process, maintenance of dose precision, limited stability in solution form and also lyophilization process for cytotoxic drugs requires exposure of healthcare professional to cytotoxic vapor of the drugs.

To overcome above mentioned problems associated with lyophilized formulation and also to enhance stability and bioavailability of active ingredient, present invention provides ready to dilute injectable pharmaceutical formulations of bortezomib with significantly improved solubility, stability/comparable stability.

OBJECT OF INVENTION

The primary object of present invention is to provide ready to dilute injectable pharmaceutical formulations of bortezomib comprises of bortezomib, non aqueous solvents or solubility enhancing agents to improve the solubility of active ingredient, bortezomib and pH adjusting agent.

Another object of present invention is to provide cost effective, easy to dilute and high patient compliance ready to dilute injectable formulations of bortezomib with improved stability.

Yet another object of present invention is to provide process of preparation of ready to dilute injectable formulations of bortezomib.

SUMMARY OF THE INVENTION

It has been found that the solubility of proteosome inhibitors, such as bortezomib, is significantly enhanced when it is formulated with non-aqueous solvents.

The present invention relates to the ready to dilute injectable formulations of bortezomib with increased solubility and stability. In one aspect, present invention relates to formulations of bortezomib with non-aqueous solvents or solubility enhancing agents with pH modifier or pH adjusting agent.

In one embodiment, the present invention is a pharmaceutical formulation that includes bortezomib and monothioglycerol.

In another embodiment, the present invention is a pharmaceutical formulation that includes bortezomib and propylene glycol with and without presence of pH modifying agent.

In another embodiment, the present invention relates to pharmaceutical formulation that comprises bortezomib, propylene glycol, vitamin E TPGS (d-α-tocopheryl polyethylene glycol 1000 succinate) and with and without presence of pH modifying agent.

In another embodiment, present invention is a pharmaceutical formulation that includes bortezomib, propylene glycol and glycerine with and without presence of pH modifying agent.

In another aspect, present invention relates to the process of preparation of the above mentioned all ready to dilute injectable formulations of bortezomib.

DETAILED DESCRIPTION OF THE INVENTION

Proteosome are the protein complexes in all eukaryotes and archaea. The main function of proteosome is to degrade unnecessary and damaged proteins by proteolysis that breaks chemical bonds.

Proteosome inhibitors are the drugs that block the action of proteosomes, cellular complexes which breakdown proteins. In vitro investigations demonstrated proteosome inhibitor have broad spectrum of anti-proliferative and pro-apoptotic activity against tumours, which makes proteosome inhibitors as potential anti-cancer agents.

The ubiquitin proteosome pathway regulates many processes in the cell which are important for tumour cell growth and survival. Targeting the ubiquitin proteosome pathway has emerged as an effective approach for treatment of human cancer.

Bortezomib is the first proteosome inhibitor anticancer drug approved for treatment of multiple myeloma, relapsed/refractory multiple myeloma and mantle cell lymphoma.

Lactacystin is the natural product which is the first non-peptidic proteosome inhibitor, while disulfiram and epigallocatechin-3-gallate are the other drugs which are proposed to be proteosome inhibitors.

Bortezomib, [(1R)-3-methyl-1-[[(2s)-3-phenyl-2-(pyrazine-2-carbonylamino)propanoyl]amino]butyl]boronic acid. Bortezomib has the following chemical structure:

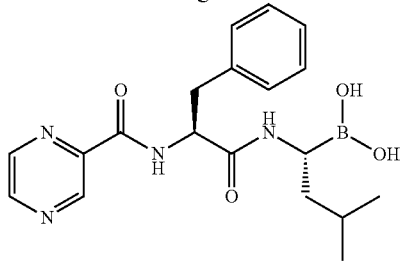

The 26S proteosome is a multiprotein complex comprised of 20S core particles and two 19S regulatory particles that degrades ubiquitinated proteins. The 26S proteosome has chymotrypsin-like activity. The boron atom in bortezomib binds to the catalytic site of 26S proteosome with high affinity and specificity. Inhibition of 26S proteosome prevents targeted proteolysis which leads to disruption of multiple signaling cascades within the cell. The disruption of normal homeostatic mechanism can lead to cell death.

Bortezomib is susceptible to oxidative degradation under any experimental conditions. Stress testing and accelerated stability studies revealed that bortezomib is unstable in aqueous solution for injection. Stability of bortezomib slightly improved in mixture of aqueous and non-aqueous solvents.

To improve stability of bortezomib lyophilized and reconstituted prior to injection formulation are designed. Lyophilized formulations are associated with several disadvantages that include time consuming reconstitution process, maintenance of dose precision, limited stability in solution form and also lyophilization process for cytotoxic drugs requires exposure of healthcare professional to cytotoxic vapour of the drugs, so other formulations with selected solvents and solubility enhancing ingredients are required to improve solubility and stability of bortezomib.

The primary object of present invention is to provide ready to dilute injectable pharmaceutical formulations of bortezomib comprises of bortezomib, non aqueous solvents and solubility enhancing agents which impart solubility and stability of active ingredient bortezomib.

Ready to dilute injectable formulations of present invention have following benefits over other liquid formulations:
1) Reconstitution of liquid formulation is not necessary.
2) Extended product stability and stability after dilution.
3) Reduction in manufacturing cost.
4) Simple manufacturing process Aspects of the present invention relates to pharmaceutical compositions comprising bortezomib for parenteral administration and process of preparation of same. In specific aspects, present invention relates to stable ready to dilute injectable pharmaceutical compositions comprising bortezomib with non-aqueous solvents and solubility enhancing ingredients such as nonionic surfactants with pH modifier.

Non-aqueous solvents can be selected from fixed oils, alcohols, glycerin, polyethylene glycol, propylene glycol, glycerin, monothioglycerol, dimethylsulfoxide, ethyl ether and liquid paraffin.

Nonionic surfactants can be selected from sorbitan esters, polysorbates, poloxamers and vitamin E TPGS.

In one embodiment, the present invention is a pharmaceutical formulation that includes bortezomib and monothioglycerol. Monothioglycerol serves as an anti oxidant and protects bortezomib from oxidative degradation. In another embodiment, the present invention is a pharmaceutical formulation that includes bortezomib and propylene glycol. Non-aqueous solvent propylene glycol increases the solubility of bortezomib with head space oxygen less than 5%.

As bortezomib degradation pathway differs in different conditions (media/vehicle, temp, light etc.) and also observed that impurity trend on stability depends on initial environment and initial and throughout situation control is required. Hence, in the present invention pH optimization trial also taken.

In another embodiment, the present invention comprises a pharmaceutical formulation composed of bortezomib, propylene glycol and hydrochloric acid to maintain the pH of formulation 1.0 to 3.0 with head space oxygen less than 5%.

In another embodiment the present invention is a pharmaceutical formulation that includes bortezomib, propylene glycol, vitamin E TPGS and hydrochloric acid to maintain pH 1.0 to 3.0 of formulation. In present formulation vitamin E TPGS increases the solubility and stability of active ingredient, bortezomib. In another embodiment, the present invention comprises of bortezomib, propylene glycol and glycerine with head space oxygen less than 5%.

In another embodiment, the present invention is a formulation of bortezomib, propylene glycol, glycerine and hydrochloric acid to maintain pH of formulations to 1.0 to 3.0 with head space oxygen less than 5%.

Other pH modifying agent: HCl, Maleic acid, Ascorbic acid, oxalic acid, Citric acid buffer, Acetate buffer, $CO_2$ purging.

Anti-oxidant: Vit-E TPGS, Monothioglycerol, L-Cysteine HCl, Sodium sulfite, L-Methionine, Di-sodium EDTA.

Process for preparation of ready to dilute injectable formulation of bortezomib comprises following steps:
(a) Set pH of non-aqueous solvent to 1.0 to 3.0 by using pH adjusting agent.
(b) Dissolve Bortezomib in above prepared mixture.
(c) Adjust the pH of mixture of step b) to 1.0 to 3.0 using pH adjusting agent.
(d) Filter the mixture of step c) and fill into vials.

For administration, it could be diluted with suitable diluents for required concentration.

Present invention has been described by way of examples only and it is recognized that modifications are falling within the scope and spirit of the appended claims, and which would be obvious for a person skilled in the art based upon the disclosure herein, are also considered to be included within the scope of this invention.

Additional objects, advantages, and novel features of this invention will become apparent to those skilled in the art upon examination of the following examples thereof, which are not intended to be limiting. In the Examples, procedures that are constructively reduced to practice are described in the present tense, and procedures that have been carried out in the laboratory are set forth in the past tense.

EXAMPLES

Drug or excipients with its range are shown below in table:

| Ingredients | Examples | | | | | |
| --- | --- | --- | --- | --- | --- | --- |
| | 1 | 2 | 3 | 4 | 5 | 6 |
| Bortezomib (mg) | 2.5-3.5 | 2.5-3.5 | 2.5-3.5 | 2.5-3.5 | 2.5-3.5 | 2.5-3.5 |
| Monothiglycerol (ml) | 0.1-1 | — | — | — | — | — |
| Propylene glycol (ml) | — | 0.1-1 | 0.1-1 | 0.1-1 | 0.1-1 | 0.1-1 |
| Vitamin E TGPS (mg) | — | — | — | 0.1-0.5 | — | — |
| Glycerine (ml) | — | — | — | — | 0.007-0.8 | 0.007-0.8 |
| Hydrochloric acid (ml) | — | — | Required to set pH of 1.0 to 3.0. | Required to set pH of 1.0 to 3.0. | — | Required to set pH of 1.0 to 3.0. |

The ready to dilute injectable formulations of above mentioned examples are prepared by following method:

Example 1 a) In this formulation bortezomib was dissolved monothioglycerol using vortex mixer.
b) Mixture was filtered and filled into the vials.
c) Further, it should be diluted with suitable diluents for required concentration for the administration.
d) Initial Trials for selection of excipients and compatibility:

| Formula: (2.5 mg Bortezomib + 1 ml Monothioglycerol) STABILITY RESULT: | | | | | | |
| --- | --- | --- | --- | --- | --- | --- |
| S. No Test parameters | Initial | 2-8 C. 1 M | 30 C. 1 M | 40 C. 10 D | 40 C. 1 M | 40 C. 3 M |
| 1 | Related Substances | | | | | |
| Impurity - G | — | — | — | — | — | — |
| Impurity - E | — | 0.30 | 0.57 | — | 0.55 | 1.32 |
| Impurity - L | — | 0.02 | 0.02 | — | 0.03 | — |
| Impurity - C + D | — | — | — | — | — | — |
| Impurity - F | — | — | — | — | 0.05 | 0.12 |
| Impurity - J + M | — | — | — | — | — | — |
| Impurity - H | — | — | — | — | — | — |
| Impurity - I | — | — | — | — | — | — |
| Impurity - A + K | — | 0.07 | 0.04 | — | 0.01 | — |
| Single Max (Unknown) | 0.08 | 0.02 | 0.02 | 0.16 | 0.01 | 0.08 |
| Total impurities | 0.18 | 0.41 | 0.66 | 0.24 | 0.65 | 1.76 |

Example 2 a) In this formulation bortezomib was dissolved in propylene glycol.
b) Mixture was filtered and filled into vials.
c) Further, it should be diluted with suitable diluents for required concentration for the administration

| Formula: (2.5 mg Bortezomib + 1 ml Propylene glycol) (pH: 4.25) STABILITY RESULT: | | | | | | |
| --- | --- | --- | --- | --- | --- | --- |
| S. No Test parameters | Initial | 2-8 C.- 1 M | 30 C.- 1 M | 40 C.- 10 D | 40 C.- 1 M | 40 C.- 3 M |
| 1 | Related Substances | | | | | |
| Impurity-G | — | — | 0.04 | — | — | — |
| Impurity - E | 0.01 | 0.01 | — | 0.06 | 0.14 | 0.76 |
| Impurity - L | — | — | — | — | — | — |
| Impurity - C + D | — | — | 0.09 | 0.30 | 0.68 | 2.86 |
| Impurity - F | 0.05 | 0.05 | 0.12 | 0.12 | 0.12 | 0.23 |
| Impurity - J + M | — | 0.01 | 0.02 | — | 0.03 | 0.08 |
| Impurity - H | — | — | — | — | 0.01 | 0.02 |

-continued

| | Formula: (2.5 mg Bortezomib + 1 ml Propylene glycol) (pH: 4.25) STABILITY RESULT: | | | | | |
|---|---|---|---|---|---|---|
| S. No Test parameters | Initial | 2-8 C.- 1 M | 30 C.- 1 M | 40 C.- 10 D | 40 C.- 1 M | 40 C.- 3 M |
| Impurity - I | — | — | — | — | 0.01 | 0.02 |
| Impurity - A + K | — | — | — | — | — | — |
| Single Max (Unknown) | 0.01 | 0.01 | 0.01 | 0.02 | 0.01 | 0.09 |
| Total impurities | 0.07 | 0.08 | 0.28 | 0.50 | 1.01 | 4.23 |

Example 3 a) The pH of propylene glycol was set 1.0 to 3.0 by using diluted HCl solution.
b) Bortezomib was dissolved in above prepared mixture.
c) The pH of mixture of step b) is adjusted to 1.0 to 3.0 using HCl solution.
d) Mixture of step c) was filtered and filled into vials.
e) Further, it should be diluted with suitable diluents for required concentration for the administration.

| | Formula: (2.5 mg Bortezomib + 1 ml Propylene glycol) (pH set 1.00 to 3.00) STABILITY RESULT | | | | | |
|---|---|---|---|---|---|---|
| S. No Test parameters | Initial | 2-8 C.- 1 M | 30 C.- 1 M | 40 C.- 10 D | 40 C.- 1 M | 40 C.- 3 M |
| 1 | Related Substances | | | | | |
| Impurity - G | — | — | — | — | — | — |
| Impurity - E | 0.01 | 0.01 | 0.02 | 0.02 | 0.11 | 0.43 |
| Impurity - L | — | — | — | — | — | — |
| Impurity - C + D | — | — | — | — | 0.06 | 0.66 |
| Impurity - F | 0.06 | 0.06 | 0.06 | 0.07 | 0.13 | 0.25 |
| Impurity - J + M | — | 0.02 | 0.03 | — | 0.07 | 0.08 |
| Impurity - H | — | — | — | — | — | 0.03 |
| Impurity - I | — | — | — | — | — | 0.03 |
| Impurity - A + K | 0.01 | 0.01 | 0.01 | 0.01 | — | — |
| Single Max (Unknown) | 0.01 | 0.01 | 0.01 | 0.04 | 0.04 | 0.12 |
| Total impurities | 0.09 | 0.11 | 0.14 | 0.21 | 0.41 | 1.71 |

Example 4 a) Vitamin E TPGS is melted first and mixed with propylene glycol.
b) Dilute HCl solution is added to maintain the pH of above prepared solution to 3.0.
c) Bortezomib was dissolved in mixture of Step b).
d) pH of mixture of step c) was adjusted to 1.0 to 3.0.
e) Mixture of step d) is filtered and filled into vials.

| | Formula: 2.5 mg Bortezomib + 1 ml propylene glycol + 0.2 mg Vitamin E TPGS STABILITY RESULT: | | | | | |
|---|---|---|---|---|---|---|
| S. No Test parameters | Initial | 2-8 C.- 1 M | 30 C.- 1 M | 40 C.- 10 D | 40 C.- 1 M | 40 C.- 3 M |
| 1 | Related Substances | | | | | |
| Impurity - G | — | — | — | — | — | — |
| Impurity - E | 0.02 | 0.01 | 0.07 | 0.07 | 0.13 | 0.35 |
| Impurity - L | — | 0.01 | — | — | — | — |
| Impurity - C + D | — | — | — | — | — | 0.21 |
| Impurity - F | 0.16 | 0.15 | — | 0.08 | — | 0.16 |
| Impurity - J + M | — | 0.06 | 0.07 | — | 0.05 | 0.10 |
| Impurity - H | 0.02 | 0.01 | 0.03 | 0.09 | 0.09 | 0.08 |
| Impurity - I | 0.01 | 0.01 | 0.06 | 0.07 | 0.11 | 0.06 |
| Impurity - A + K | 0.20 | 0.09 | — | 0.24 | — | — |
| Single Max (Unknown) | 0.04 | 0.03 | 0.22 | 0.12 | 0.17 | 0.17 |
| Total impurities | 0.54 | 0.40 | 0.75 | 0.97 | 0.86 | 1.39 |

Further, it should be diluted with suitable diluents for required concentration for the administration

Example 5 a) The pH of glycerin was set 1.0 to 3.0 by using diluted HCl solution.
b) Bortezomib was dissolved in propylene glycol.
c) Glycerine was added to the solution of step a) and mixed uniformly.
d) Mixture of step c) is filtered and filled into vials.

Formula: Bortezomib 3.5 mg + 30 mg PG + 373 mg Glycerin
STABILITY RESULT:

| S. No | Test parameters | Initial | 40/75_1M | 40/75_2M | 40/75_3M | 40/75_6M |
|---|---|---|---|---|---|---|
| 1 | Related Substances (After withdrawal of sample from stability chamber → Reconstitution to 1 mg/mL using Normal saline → Analysis) | | | | | |
| | Impurity - A (or Imp-K) | — | — | — | — | — |
| | Impurity - C (or Imp-D) | 0.03 | 0.02 | 0.01 | 0.04 | 0.92 |
| | Impurity - G | — | — | — | — | — |
| | Impurity - L | — | — | 0.02 | 0.02 | — |
| | Impurity - E | 0.03 | 0.14 | 0.17 | 0.29 | 0.61 |
| | Impurity - F | — | — | — | — | — |
| | Impurity - H | — | — | — | — | — |
| | Impurity - I | — | — | — | — | — |
| | Impurity - J (or Imp-M) | — | — | — | — | — |
| | Single Max (Unknown) | 0.08 | 0.11 | 0.16 | 0.18 | 0.46 |
| | Total impurities | 0.20 | 0.41 | 0.66 | 0.88 | 2.67 |

Further, it should be diluted with suitable diluents for required concentration for the administration

Example 6 a) The pH of propylene glycol was set 1.0 to 3.0 by using diluted HCl solution.
b) Bortezomib was dissolved in prepared mixture.
c) pH of mixture of step b) was adjusted to 1.0 to 3.0.
d) Mixture of step c) is filtered and filled into vials.

Formula: 0.5 ml PG (pH: 1.00-3.00) + Bortezomib 3.5 mg
STABILITY RESULT:

| S. No | Test parameters | Initial | 40/75 1 M | 40/75 2 M | 40/75 3 M | 40/75 6 M | 25/60 6 M | 25/60 12 M | 30/65 6 M | 30/65 12 M | 2-8° C. 12 M |
|---|---|---|---|---|---|---|---|---|---|---|---|
| 1 | Assay | 101.40 | 98.30 | 96.20 | 93.60 | 92.00 | 98.00 | 89.60 | 95.20 | 86.50 | NP |
| 3 | Related Substances | | | | | | | | | | |
| | Impurity - G | — | — | — | — | — | — | — | — | — | — |
| | Impurity - E | — | 0.04 | 0.12 | 0.25 | 1.12 | 0.03 | 0.07 | 0.11 | 0.24 | 0.01 |
| | Impurity - L | — | 0.03 | 0.08 | 0.08 | 0.25 | 0.01 | 0.04 | 0.05 | 0.08 | — |
| | Impurity - C + D | — | 0.10 | 0.66 | 1.29 | 5.13 | 0.05 | 0.16 | 0.44 | 0.41 | 0.01 |
| | Impurity - F | 0.04 | 0.06 | 0.10 | 0.19 | 0.37 | 0.10 | 0.13 | 0.18 | 0.21 | 0.06 |
| | Impurity - J + M | 0.05 | 0.16 | 0.28 | 0.21 | 0.32 | 0.17 | 0.18 | — | 0.20 | 0.09 |
| | Impurity - H | — | 0.02 | 0.01 | 0.01 | 0.03 | — | 0.03 | — | 0.04 | — |
| | Impurity - I | — | — | 0.01 | 0.01 | 0.04 | — | 0.01 | — | 0.02 | — |

-continued

Formula: 0.5 ml PG (pH: 1.00-3.00) + Bortezomib 3.5 mg
STABILITY RESULT:

| S. No | Test parameters | Initial | 40/75 | | | | 25/60 | | 30/65 | | 2-8° C. |
|---|---|---|---|---|---|---|---|---|---|---|---|
| | | | 1 M | 2 M | 3 M | 6 M | 6 M | 12 M | 6 M | 12 M | 12 M |
| | Impurity - A + K | — | — | — | — | — | — | — | — | — | — |
| | Single Max (Unknown) | — | — | 0.03 | 0.03 | 0.07 | 0.02 | 0.05 | — | — | — |
| | Total impurities | 0.09 | 0.41 | 1.29 | 2.07 | 7.58 | 0.38 | 0.72 | 1.00 | 1.66 | 0.17 |

Further, it should be diluted with suitable diluents for required concentration for the administration.

Concentrated product diluted to 1 mg/ml using normal saline and tested stability. In compare with VELCADE currently available as Approved Drug in USA and Europe. Where, reconstituted solution should be administered within 8 hours of preparation. When reconstituted as directed, VELCADE may be stored at 25° C. (77° F.). The reconstituted material may be stored in the original vial and/or the syringe prior to administration. The product may be stored for up to 8 hours in a syringe; however, total storage time for the reconstituted material must not exceed 8 hours when exposed to normal indoor lighting. The composition shows improved stability when stored at 25° C. as shown in the below table.

| | Condition | | | |
|---|---|---|---|---|
| | Reconstitute With NS_A/0 Hr | Reconstitute With NS_A/4 Hr | Reconstitute With NS_A/8 Hr | Reconstitute With NS_A/12 Hr |
| TRF No. | 16/2365 | 16/2365 | 16/2365 | 16/2365 |
| Name of Impurity | % Area | % Area | % Area | % Area |
| Impurity-A (or Imp-K) | — | — | — | — |
| Impurity-C (or Imp-D) | 0.90 | 0.91 | 0.90 | 0.90 |
| Impurity-G | — | — | — | — |
| Impurity-L | 0.04 | 0.04 | 0.04 | 0.04 |
| Impurity-E | 0.08 | 0.08 | 0.08 | 0.08 |
| Impurity-F | 0.16 | 0.16 | 0.16 | 0.16 |
| Impurity-H | — | 0.01 | — | 0.01 |
| Impurity-I | — | — | — | — |
| Impurity-J (or Imp-M) | 0.13 | 0.15 | 0.14 | 0.15 |
| Single max unknown | 0.07 | 0.08 | 0.07 | 0.07 |
| Total imp. | 1.44 | 1.49 | 1.45 | 1.47 |

The ready to dilute injectable compositions of the present invention are used for the treatment of multiple myeloma. Bortezomib has proven to be safe and effective in patients with relapsed and or refractory multiple myeloma. Bortezomib also exhibits clinical benefits with manageable toxicities and improve the duration of response and survival of patients.

Also Local tolerability/tissue reaction of Bortezomib 3.5 mg/0.2 mL compared with Velcade (Reference product) in Female New-Zealand White Rabbits.

The study was conducted to assess the local tolerance of Bortezomib in comparison with Velcade (Reference product) in New Zealand White Rabbits by single subcutaneous or intravenous route.

No mortality or morbidity was observed in any of the groups. Body weight changes were normal in the treated group.

External observation of the site of injection did not reveal any signs of local intolerance when the test item, Bortezomib or the reference item, Velcade was administered by either subcutaneous or intravenous route.

Microscopically, test item, Bortezomib and Velcade showed no signs of local intolerance when injected intravenously.

However, when administered through subcutaneous route signs of local intolerance was observed microscopically in 50% of animals treated with reference item, Velcade and 25% of animals treated with test item, Bortezomib.

In the light of above findings, Bortezomib did not cause any local intolerance when administered intravenously. Local intolerance observed at the injection site of subcutaneously treated rabbits were comparable with the reference product treated animals.

Further, bortezomib also have promising activity in combination with other cytotoxic agents.

The composition comprising above said ingredients can also be used in topical dosage form like transdermal patch.

The foregoing discussion of the invention has been presented for purposes of illustration and description. The foregoing is not intended to limit the invention to the form or forms disclosed herein. Although the description of the invention has included description of one or more embodiments and certain variations and modifications, other variations and modifications are within the scope of the invention, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter. All references cited herein are incorporated by reference in their entirety.

What is claimed is:

1. A composition for a ready to dilute injectable pharmaceutical formulation of bortezomib said composition consisting of (i) bortezomib in the range from 7.0 mg/mL to 17.5 mg/mL, (ii) a non-aqueous solvent, (iii) a non-buffer pH modifying or pH adjusting agent, and (iv) optionally an anti-oxidant, wherein an individual impurity present in said composition is less than 2.0% and the total amount of impurities present in said composition is less than 5.0%.

2. The composition of claim 1, wherein said composition contains said anti-oxidant.

3. The composition of claim 1, wherein said non-aqueous solvent is selected from the group consisting of a fixed oil, an alcohol, glycerin, polyethylene glycol, propylene glycol, monothioglycerol, dimethylsulfoxide, ethyl ether, liquid paraffin, and a combination thereof.

4. The composition of claim 1, wherein said pH modifying or pH adjusting agent is selected from the group consisting of hydrochloric acid, maleic acid, ascorbic acid, oxalic acid, carbonic acid, and a combination thereof.

5. The composition of claim 2, wherein said anti-oxidant is selected from the group consisting of d-α-tocopheryl polyethylene glycol 1000 succinate ("Vitamin-E TPGS"), monothioglycerol, L-cysteine hydrochloride, sodium sulphite, L-methionine, disodium EDTA, and a combination thereof.

6. The composition of claim 4, wherein said pH modifying or pH adjusting agent comprises hydrochloric acid.

7. The composition of claim 1, wherein pH of said composition is in the range from pH 1.0 to pH 3.0.

* * * * *